(12) United States Patent
Gao et al.

(10) Patent No.: US 12,202,736 B2
(45) Date of Patent: Jan. 21, 2025

(54) PREPARATION METHOD OF PHOTO CATALYST BY TRANSITION METAL HALIDE MOLTEN SALT AND USE THEREOF

(71) Applicant: Linyi University, Linyi (CN)

(72) Inventors: Shanmin Gao, Linyi (CN); Zunfu Hu, Linyi (CN); Jiajia Wang, Linyi (CN)

(73) Assignee: LINYI UNIVERSITY, Linyi (CN)

( * ) Notice: Subject to any disclaimer, the term of this patent is extended or adjusted under 35 U.S.C. 154(b) by 320 days.

(21) Appl. No.: 17/875,754

(22) Filed: Jul. 28, 2022

(65) Prior Publication Data

US 2023/0264971 A1 Aug. 24, 2023

(30) Foreign Application Priority Data

Feb. 24, 2022 (CN) .......................... 202210172367.6

(51) Int. Cl.
| | |
|---|---|
| C01G 23/00 | (2006.01) |
| B01D 53/00 | (2006.01) |
| B01D 53/86 | (2006.01) |
| B01J 21/06 | (2006.01) |
| B01J 35/39 | (2024.01) |
| B01J 37/12 | (2006.01) |
| C01G 23/053 | (2006.01) |
| C02F 1/30 | (2023.01) |
| C02F 1/72 | (2023.01) |
| C02F 101/30 | (2006.01) |

(52) U.S. Cl.
CPC ......... *C01G 23/053* (2013.01); *B01D 53/007* (2013.01); *B01D 53/86* (2013.01); *B01J 21/063* (2013.01); *B01J 35/39* (2024.01); *B01J 37/12* (2013.01); *C02F 1/30* (2013.01); *C02F 1/725* (2013.01); *B01D 2255/802* (2013.01); *C02F 2101/30* (2013.01); *C02F 2305/10* (2013.01)

(58) Field of Classification Search
None
See application file for complete search history.

(56) References Cited

U.S. PATENT DOCUMENTS

2018/0318795 A1* 11/2018 Yu .......................... C01G 49/06
2020/0255298 A1*  8/2020 Yang ..................... C09C 1/3653

* cited by examiner

*Primary Examiner* — Stefanie J Cohen
(74) *Attorney, Agent, or Firm* — McClure, Qualey & Rodack, LLP

(57) ABSTRACT

A preparation method of photo catalyst by transition metal halide molten salt and use thereof, wherein low-valence titanium complexes stable in air and water are used as a Ti source, transition metal halide is used as molten salt, mixing the Ti source and the molten salt as per a certain mole ratio and grinding, heating at air atmosphere until no lower than a fusion point of the molten salt, keeping the molten salt in a state of melting, maintaining the temperature, washing with water, and reduced $TiO_{2-x}$ rich in $Ti^{3+}$ and Ov is obtained in one-step melting reaction. Deficiencies that multiple steps are involved for preparing conventional defect titanium dioxide or use of inflammable and explosive reducing gases or other dangerous reducing agents or oxidizing agents have been addressed; and the defect that the Ti source is liable to be dissolved in organic and other solvents is fully avoided.

7 Claims, 7 Drawing Sheets

PREPARATION METHOD OF PHOTO CATALYST BY TRANSITION METAL HALIDE MOLTEN SALT AND USE THEREOF

TECHNICAL FIELD

The present invention belongs to the technical field of catalysts, especially a preparation method of photo catalyst by transition metal halide molten salt and use thereof.

BACKGROUND TECHNOLOGY

Currently, titanium dioxide ($TiO_2$) has become the most researched photo catalyst due to properties of being of excellent thermal and chemical stability, good photochemical performance and appropriate valence band (VB) and conduction band (CB) positions. However, $TiO_2$ can only be excited by ultraviolet light with a wavelength of less than 387 nm due to broad band gap thereof (3.2 eV for anatase and 3.0 eV for rutile). As ultraviolet light occupies only 5% of sun light, application of $TiO_2$ in visible lights is limited significantly; therefore, modification of $TiO_2$ is always a hot spot for researches.

By introducing $Ti^{3+}$ and oxygen vacancy (Ov) defects, reduced $TiO_2$ ($TiO_{2-x}$) is formed, a photo absorption range of $TiO_2$ can be extended, and electric conductivity of $TiO_2$ can be improved too, which is contributive to separation between photo-induced electrons and vacancies, so that photo catalysis performance of $TiO_2$ can be enhanced greatly and $TiO_2$ can be used in photo catalysis, sterilization and disinfection. At present, preparation methods of $TiO_{2-x}$ comprise primarily: (1) reduction by hydrogen and carbon monoxide; (2) thermal reduction by active metals; (3) reduction by metal hydride; (4) reduction by organic and mineral molecules (imidazole, ascorbic acid and hydrazine hydrate etc.); (5) thermal treatment under vacuum or inert air; (6) laser ablation; (7) plasma methods; and (8) chemical oxidation etc. However, for reduction, usually common $TiO_2$ is used as raw materials, and reduction treatment is carried out in different conditions, reduction usually undergoes a process of from surfaces of $TiO_2$ to centers thereof, the $Ti^{2+}$ and Ov obtained are usually at the surfaces of $TiO_2$ particles, and are liable to be oxidized by dissolved oxygen in the air and water, thereof, stability of $TiO_2$ obtained is relatively poor. In the meanwhile, it seems to be not possible to avoid insufficient or excess oxidation. Furthermore, reduction by $H_2$ or metal hydride and nitride usually need shielding of inert gases, which is costly and involves complex technologies and is not suitable for batch processing and application. By preparing $Ti^{3+}$ self-doping $TiO_2$ by thermal treatment foreign matters in raw materials can be removed effectively, however, usually high temperature is required, and the product is rutile, and when the thermal treatment temperature is low, anatase $TiO_2$ with not very good crystalline is obtained, further, charge carrier recombination centers are generated, and during thermal treatment a waste of energy is severe. Although when preparing $Ti^{3+}$ self-doping $TiO_2$ by laser ablation and plasma methods quantity of $Ti^{3+}$ and Ov can be adjusted by adjusting power of laser and plasma, it is necessary to use special laser and plasma devices, therefore, preparing $Ti^{3+}$ self-doping $TiO_2$ with the present method is not popular.

Molten salt synthesis is an inorganic material synthesizing method and is a simple method for preparing nanometer and micrometer grade powder materials at a relatively low temperature and short reaction time. Recently, with deepening of researches, advantages of molten salt synthesis are gradually shown, application thereof is wider and wider, and a plurality of oxidant powders have been obtained. By the molten salt synthesis method, salt and reacting substances are weighed as per a certain ratio, mixed evenly and molten by heating and the reacting substances react in molten salt. After reaction, cool down the molten salt, dissolve the salt with appropriate solvents and upon filtering and washing synthesized products can be obtained. Synthesizing oxidant materials by molten salt is characterized in low synthesis temperature, easy operation, even chemical substances in synthesized powders and good crystalline appearances. For example, M. V. Reddy et al obtained pure $TiO_2$ using $TiOSO_4 \cdot xH_2SO_4 \cdot xH_2O$ as a source of Ti, in mixed molten salt of $NaNO_3/KNO_3/LiNO_3$ and LiCl, reacting at 510° C. for 30 mins or reacting at 280° C. for 2 h, or maintaining temperature at 180° C. for 2 h in mixed molten salt of $LiNO_3$ and LiOH. Changhua Wang et al obtained Nb doped $TiO_2$ with commercial P25 $TiO_2$ as raw materials, in mixed molten salt of NaCl and $Na_2HPO_4 \cdot 12H_2O$, adding $Nb_2O_5$, and maintaining temperature and reacting for 8 h at 825° C. A patent with a filing number of CN 2017105660016 entitled "preparation method of fluorine and nitrogen co-doped monocrystalline mesoporous $TiO_2$ catalyst material by molten salt", first of all, tetrabutyl titanate, carbamide and hydrofluoric acid are used as respectively a titanium source, a fluorine source and a nitrogen source, preparing a precursor of the $TiO_2$ material by a hydro-thermal method, adding mixed nitrate as a supplemental titanium source and a morphology modifier, adding mixed nitrate molten salt and fluorine and nitrogen co-doped monocrystalline mesoporous $TiO_2$ catalyst materials are obtained. A patent with a filing number of CN 2017106272338 entitled "preparation method of boron nitride co-doped monocrystalline mesophorous $TiO_2$ catalyst materials by mixed nitrate molten salt method", wherein tetrabutyl titanate is taken as raw materials, boric acid is used as a boron source dopant, $TiO_2$ made by hydro-thermal methods is used as a precursor of the material, mixed nitrate is used as a nitrogen source and latent solvent and nitrogen boron co-doped monocrystalline mesoporous $TiO_2$ catalyst materials are made by the nitrate molten salt method.

By the foregoing analysis, problems and deficiencies of the prior art are:

(1) Among methods for preparing $TiO_2$ by molten salt currently available, either a precursor of $TiO_2$ is first prepared, and then crystallization and doping treatment is done in molten salt, or commercial $TiO_2$ is used as a precursor, and doping treatment is done in molten salt, a lot of steps are required, temperature required for doping treatment is high and energy consumption is high too.

(2) Among $TiO_2$ modification methods currently available— ion doping, introduction of tramp elements can reduce a band gap of $TiO_2$, improve utilization of visible lights, however, it will also cause thermal instability, and many charge carrier recombination centers are formed, and separation efficiency of photo-induced electrons and oxygen vacancies is reduced.

(3) Among preparation methods of $TiO_{2+x}$ currently available, usually $T^{3+}$ and Ov prepared by reduction methods are located at surfaces of $TiO_2$ particles and liable to be oxidized by dissolved oxygen in air and water, therefore, stability of them are poor, in the meanwhile, it seems that insufficient or over reduction is not avoidable; among methods for preparing $TiO_{2-x}$ currently available, for reduction with $H_2$ or metal hydride or metal nitride usually inert gases are needed for protection, which is costly, involves complex processes and is not suitable for large batch processing and use.

(4) Among methods for preparing $Ti^{3+}$ self-doped $TiO_2$ by thermal treatment, usually high temperature is required, the products are usually rutile, when thermal treatment temperature is low, anatase $TiO_2$ with very good crystalline is obtained, consequently charge carrier recombination centers are generated, and energy waste during thermal treatment is serious; and among methods for preparing $Ti^{3+}$ self-doped $TiO_2$ by laser ablation and plasma methods, special laser and plasma equipment is to be used, therefore at present preparing of $Ti^{3+}$ self-doped $TiO_2$ with the present method is not popular.

Difficulties in addressing the foregoing problems and deficiencies are that: currently, for preparation of reduced titanium dioxide photo catalysts, first of all, very expensive reaction devices are used, secondly, the reaction processes are complex, the reaction time is long or dangerous reducing gases are used, which has increased cost for preparing the materials and is not contributive to industrialization thereof. What's more, by preparing titanium dioxide by molten salt, it is not possible to obtain directly oxide state titanium dioxide and when doping with molten salt, unavoidably thermal instability caused by doping occurs, and many charge carrier recombination centers are formed and consequently, separation efficiency of photo-induced electrons and oxygen vacancies is reduced. Significances in solving the foregoing problems and deficiencies are that: by choosing Ti sources that are stable in air and water and preparing reduced titanium dioxide with excellent response capability to visible lights in one step, catalysis and degradation of pollutants by visible lights can be fully utilized. In addition, the Ti sources being stable to water and air can facilitate operations during preparation, and is thus contributive to industrialization thereof.

SUMMARY OF INVENTION

To address the problem existing in the prior art, embodiments disclosed in the present invention provide a preparation method of reduced titanium dioxide photo catalyst by transition metal halide molten salt. And technical solutions of the present invention are as following:

The present invention is realized in the following manner, a preparation method of reduced titanium dioxide photo catalyst by transition metal halide molten salt, comprising:

Using low-valence complexes stable in air and water as a Ti source, using transition metal halide as molten salt, mixing the Ti source and the molten salt as per a mole ratio, grinding, heating in air atmosphere until no less than a fusion point of the molten salt, keeping the transition metal halide in a molten state; maintaining the temperature for 2-8 h, separating by washing with water, and a reduced $TiO_{2-x}$ photo catalyst with an excellent visible response capability is obtained.

In an embodiment, the low-valence complexes stable in air and water are any one or combination of $TiH_2$, TiO, $Ti_2O_3$ and TiCN, the transition metal halide is any one or combination of CuCl, CuBr, $ZnBr_2$, $FeCl_3$, $CoCl_2$ and $CoBr_2$.

In an embodiment, the Ti source and the molten salt are mixed at a mole ratio of 1:1-1:8.

In an embodiment, a preparation method of reduced titanium dioxide photo catalyst by transition metal halide molten salt comprises following steps:

Step 1: weighing the Ti source and the transition metal halide, mixing and grinding fully in a mortar, transferring the same to a melting pot, putting into a muffle furnace, heating to 430-600° C. at a certain heating rate;

Step 2: maintaining the temperature for a certain period of time, turning off power supply, furnace cooling until reaching ambient temperature, taking out the melting pot, putting hot water in, treating by ultrasonic treatment or mixing; and Step 3: filtering and washing a product, vacuum drying, and reduced $TiO_{2-x}$ is obtained.

In an embodiment, the Ti source in the step 1 is TiO, a quantity weighed is 1 g; the transition metal halide is CuCl, a quantity weighed is 4 g; the mixing and grinding time is 10-30 minutes and the heating rate is 2-10° C./min;

In an embodiment, in the step 2, time for maintaining the temperature is 2-8 h, and temperature of the hot water is 40-80° C.;

In the step 2, treating by ultrasonic treatment or mixing comprises: treating by ultrasonic treatment for 10-30 minutes in an ultrasonic washing machine with a frequency of 25 kHz-130 kHz or mixing magnetically and dissolving for 10-30 minutes at a mixing rate of no less than 100 r/min.

In the step 3, filtering and washing comprises: filtering the product in a common way or in vacuum, separating the product and aqueous solution of the molten salt, and washing for 3-6 times with distilled water during filtering.

In the step 3, a temperature for vacuum drying is 30-120° C. and time for vacuum drying is 2-12 h.

In an embodiment, TiO is replaced with $TiH_2$, $Ti_2O_3$ and TiCN, a mass of CuCl varies from 2 g to 8 g, and can be replaced with CuBr, $ZnBr_2$, $FeCl_3$, $CoCl_2$, and $CoBr_2$, and lowest temperature after heating shall be no lower than a fusion point of corresponding molten salt, no higher than a boiling point or decomposition temperature thereof; when CuCl is chosen as the molten salt, the lowest temperature after heating shall be no less than 426° C., and the highest temperature no higher than 1490° C.; when $ZnBr_2$ is chosen as the molten salt, the lowest temperature after heating shall be no less than 395° C. and the highest temperature no higher than 650° C.; time for maintaining the temperature is 2-8 h, CuCl and CuBr shall be mixed and washed in hot water and other molten salts can be mixed in water of ambient temperature and have the molten salts dissolved or dissolution can be expedited under ultrasonic conditions.

Another purpose of the present invention is to provide the reduced titanium dioxide photo catalyst by transition metal halide molten salt obtained by the foregoing preparation method of reduced titanium dioxide photo catalyst by transition metal halide molten salt.

Another purpose of the present invention is to provide use of the reduced titanium dioxide photo catalyst by transition metal halide molten salt in catalyzing and degrading organic pollutants in waste water and waste gases under sunlight. Another purpose of the present invention is to provide use of the reduced titanium dioxide photo catalyst by transition metal halide molten salt in water treatment and disinfection, sterilization and treatment of indoor air.

In view of all the foregoing technical solutions, advantages and positive effects of the present invention are: in the preparation method of reduced titanium dioxide photo catalyst by transition metal halide molten salt provided in the present invention, low-valence titanium complexes stable in air and water are used as a Ti source, designated transition metal halide is used as molten salt, and reduced $TiO_{2-x}$ rich in $Ti^{3+}$ and Ov is obtained in one-step melting reaction.

In the present invention, deficiencies of the prior art that a lot of steps are involved for preparing conventional defect titanium dioxide or use of other dangerous reducing agents or oxidizing agents have been addressed; and the Ti source used is stable in air and water, the defect that the Ti source is liable to be dissolved in organic and other solvents is fully avoided, which is beneficial to industrialization thereof.

The product obtained in the present invention has very good visible light response capability, can be used for degrading organic pollutants in waste water and waste gases under sunlight by photo catalysis, possesses very good disinfection and sterilization functions and can be used in water treatment and disinfection and sterilization treatment of indoor air.

It shall be understood that the foregoing general description and the detailed description in the following part are only exemplary and serve for explaining purposes, rather than limiting disclosure of the present invention.

BRIEF DESCRIPTION OF DRAWINGS

The drawings are incorporated in the specification and form a part of the specification, wherein embodiments of the present disclosure are given, and are used together with the specification for explaining principles of the present disclosure.

EMBODIMENTS

To make the purposes, features and advantages of the present invention more obvious, hereinafter a detailed description will be given to embodiments of the present invention in conjunction with accompanying drawings. In the following description, many specific details are set forth for full understanding of the present invention. However, the present invention can be realized in many other ways different from those described here, those of ordinary skill in the art can make modifications without departing from principles of the present invention, thus the present invention is not limited by the following specific embodiments. Targeting at problems existing in the prior art, the present invention provides a preparation method for reduced titanium dioxide photo catalyst by transition metal halide molten salt, hereinafter the present invention will be described in detail in conjunction with the accompanying drawings.

Figure 1:
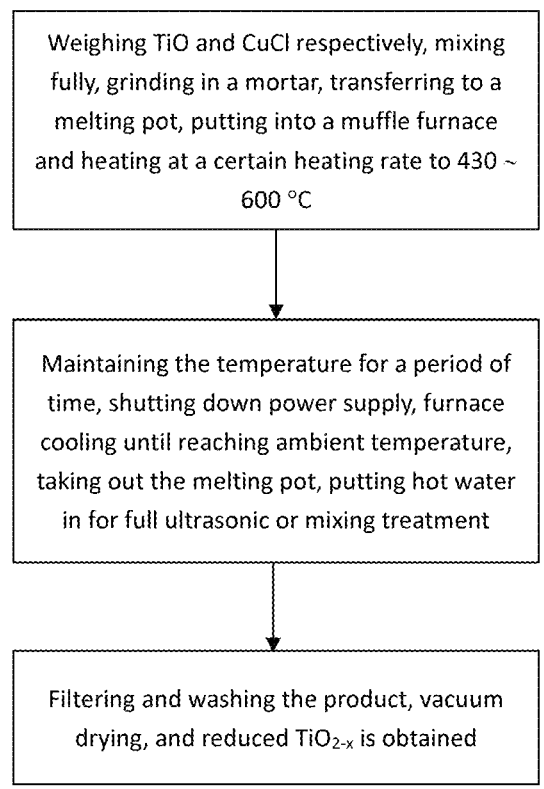
FIG. 1 is a flowchart diagram showing the preparation method of reduced titanium dioxide photo catalyst by transition metal halide molten salt provided in an embodiment of the present invention.

As shown in FIG. 1, a preparation method of reduced titanium dioxide photo catalyst by transition metal halide molten salt provided in the present invention, comprises the following steps:

S101: weighing TiO and CuCl respectively, mixing fully and grinding in a mortar, transferring the same to a melting pot, putting into a muffle furnace, heating at a certain heating rate to 430~600° C.;

S102: maintaining the temperature for a certain period of time, shutting down power supply, furnace cooling until ambient temperature, taking out the melting pot, adding hot water for full ultrasonic or mixing treatment; and S103: filtering and washing a product, vacuum drying the same and reduced $TiO_{2-x}$ is obtained.

Hereinafter the technical solutions in the present invention will be further described in conjunction with some embodiments.

Usually among methods for preparing $TiO_2$ or doped $TiO_2$ by molten salt, usually $TiOSO_4$ or $Ti(SO_4)_2$ are used as a Ti source, and alkali metal halide and phosphate such as composites of NaCl, KCl, $Na_2HPO_4$, and $K_2HPO_4$, are used as molten salt, pure $TiO_2$ is obtained, or pure $TiO_2$ is used as a Ti source, add other complexes in the molten salt to obtain doped $TiO_2$. With the former method only pure $TiO_2$ can be obtained, and the Ti source is liable to hydrolyze and during mixing and grinding influence of water shall be avoided. With the latter method, usually two-step reaction is required, that is, first of all prepare and obtain $TiO_2$ and then conduct doping reaction in molten salt.

In the present invention, low-valence complexes such as $TiH_2$, TiO, $Ti_2O_3$, and TiCN are used as a Ti source, any one or combination of transition metal halides such as CuCl (with a fusion point 426° C.), CuBr (492° C.), $ZnBr_2$ (394° C.), $FeCl_3$ (308° C.), $CoCl_2$ (724° C.) and $CoBr_2$ (678° C.) are used as molten salt, mix the Ti source and the molten salt as per a mole ratio of 1:1 to 1:8 and grind the same, heat at air atmosphere until no less than the fusion point of the molten salt, keep the transition metal halide in a state of melting, maintaining the temperature for 2-8 h, separate by washing with water, and reduced $TiO_{2-x}$ photo catalyst rich in $Ti^{3+}$ and Ov with excellent visible light response capability can be obtained.

Typical Preparation Processes:

Weigh TiO 1 g and CuCl 4 g, mixing fully and grind in a mortar for 10-30 minutes, transfer to a melting pot, put the same into a muffle furnace, heat at a heating rate of 2-10° C./min until the temperature is 430-600° C., maintain the temperature or 2-8 h, shut down power supply, furnace cool until ambient temperature, take out the melting pot, put hot water at 40-80° C. for full ultrasonic or mixing treatment (in order to expedite dissolution of CuCl, as CuCl is not soluble in cold water), filter, wash, vacuum dry at ambient temperature for 2-12 h, and reduced $TiO_{2-x}$ is obtained.

In the foregoing preparation processes, TiO can be replaced with $TiH_2$, $Ti_2O_3$, and TiCN, a mass of CuCl can vary from 2 g to 8 g, TiO can also be replaced with CuBr (492° C.), $ZnBr_2$ (394° C.), $FeCl_3$ (308° C.), $CoCl_2$ (724° C.) and $CoBr_2$ (678° C.), and the lowest temperature after heating shall be no lower than the fusion point of corresponding molten salts. Time for maintaining the temperature is 2-8 hours, CuCl and CuBr shall be washed with water and the others can be mixed at ambient temperature or treated by ultrasonic washing.

Figure 2:
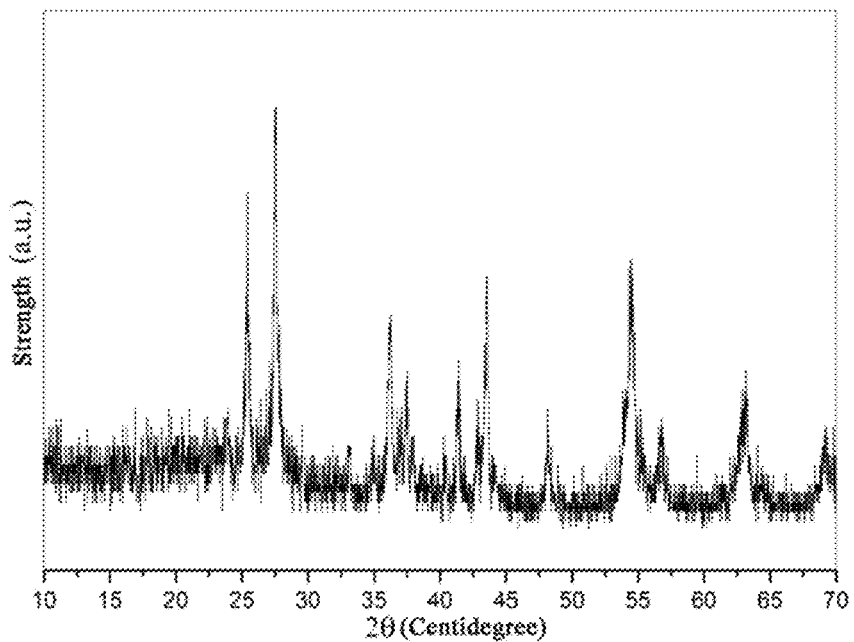
FIG. 2 is an XRD pattern showing a product obtained by reacting 4 h at 450° C. using $TiH_2$ as a Ti source, CuCl as molten salt, wherein a mass ratio between $TiH_2$ and CuCl is 1:4.

FIG. 2 is an XRD pattern showing a product obtained by reacting 4 h at 450° C. using $TiH_2$ as a Ti source, CuCl as molten salt, wherein a mass ratio between $TiH_2$ and CuCl is 1:4.

Figure 3:
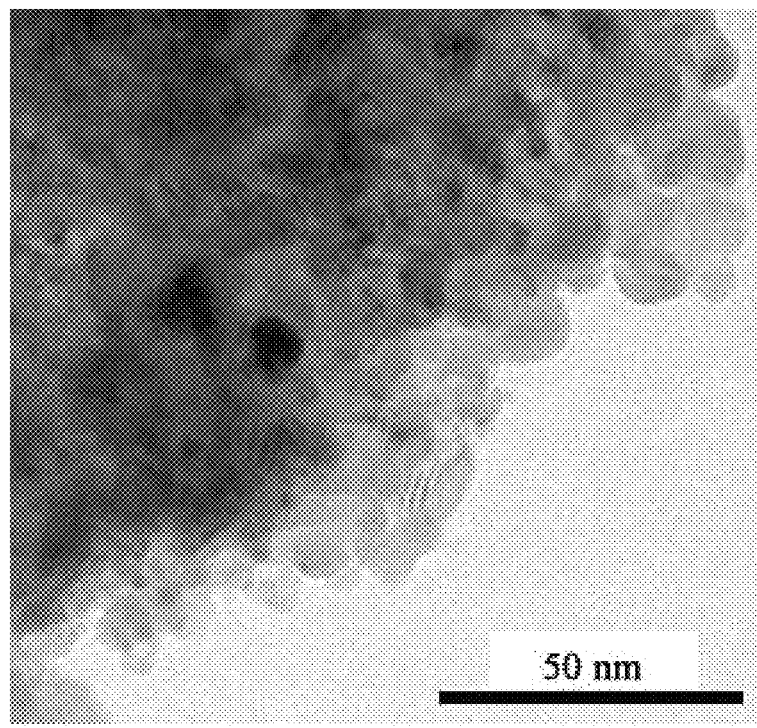
FIG. 3 is a TEM image of the product obtained by reacting 4 h at 450° C. using $TiH_2$ as a Ti source and CuCl as molten salt, wherein a mass ratio between $TiH_2$ and CuCl is 1:4.

FIG. 3 is a TEM image of the product obtained by reacting 4 h at 450° C. using $TiH_2$ as a Ti source and CuCl as molten salt, wherein a mass ratio between $TiH_2$ and CuCl is 1:4.

Figure 4:
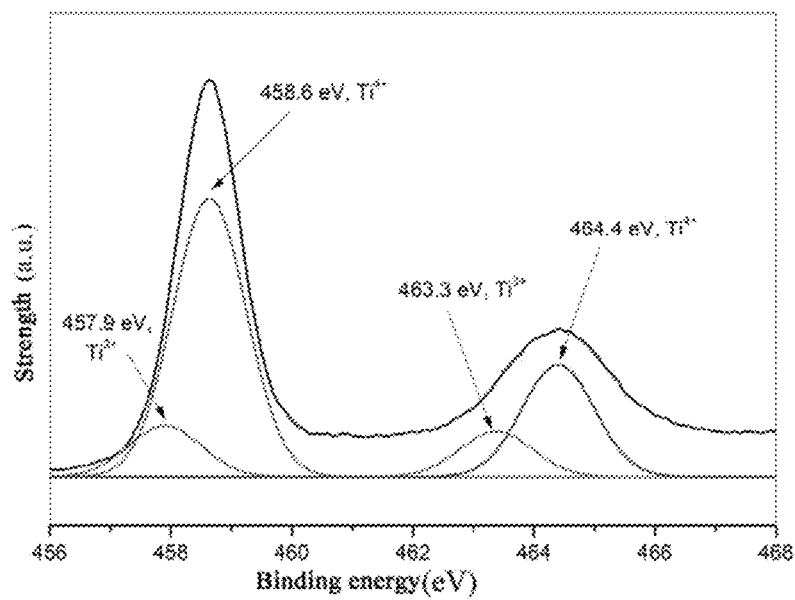
FIG. 4 is a diagram showing Ti 2p XPS results of the product obtained by reacting 4 h at 450° C. using $TiH_2$ as a Ti source and CuCl as molten salt, wherein a mass ratio between $TiH_2$ and CuCl is 1:4.

FIG. 4 is a diagram showing Ti 2p XPS results of the product obtained by reacting 4 h at 450° C. using $TiH_2$ as a Ti source and CuCl as molten salt, wherein a mass ratio between $TiH_2$ and CuCl is 1:4.

Figure 5:
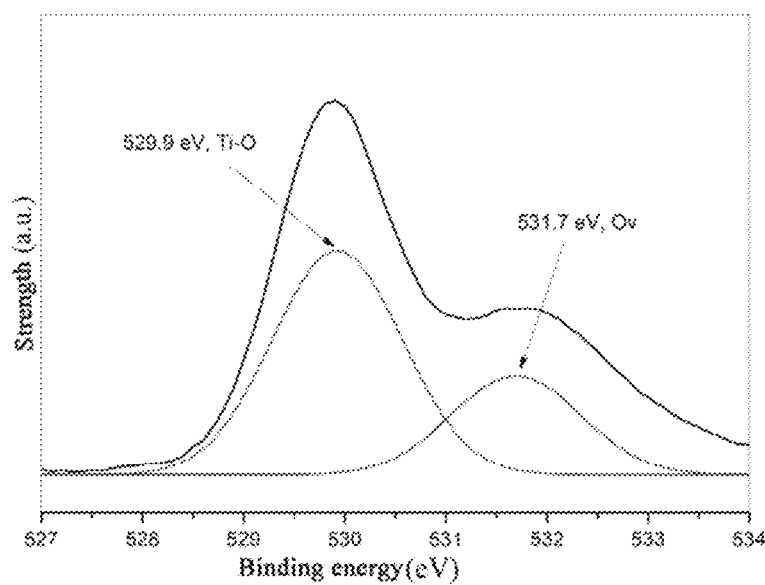
FIG. 5 is a diagram showing O1s XPS results of the product obtained by reacting 4 h at 450° C. using $TiH_2$ as a Ti source and CuCl as molten salt, wherein a mass ratio between $TiH_2$ and CuCl is 1:4.

FIG. 5 is a diagram showing O1s XPS results of the product obtained by reacting 4 h at 450° C. using $TiH_2$ as a Ti source and CuCl as molten salt, wherein a mass ratio between $TiH_2$ and CuCl is 1:4.

Figure 6:
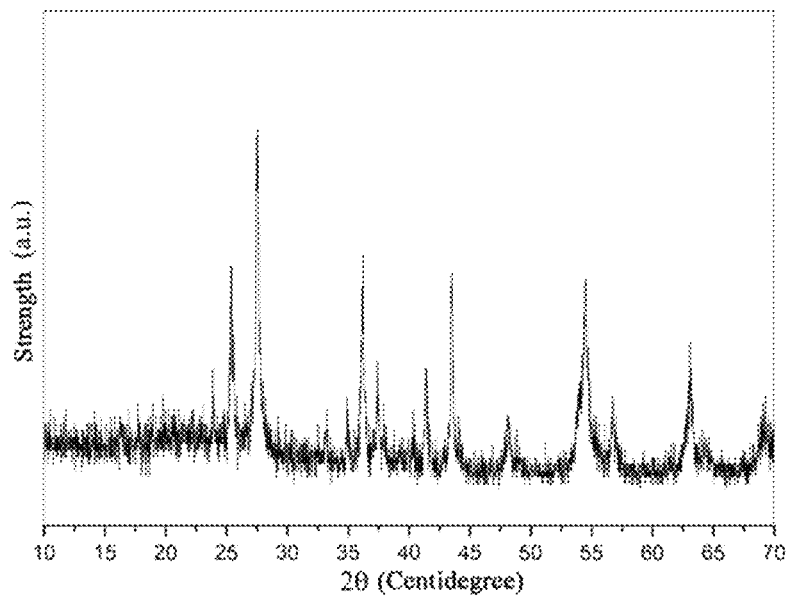
FIG. 6 is an XRD pattern showing the product obtained by reacting 4 h at 500° C. using TiO as a Ti source and CuCl as molten salt, wherein a mass ratio between TiO and CuCl is 1:6.

FIG. 6 is an XRD pattern showing the product obtained by reacting 4 h at 500° C. using TiO as a Ti source and CuCl as molten salt, wherein a mass ratio between TiO and CuCl is 1:6.

Figure 7:
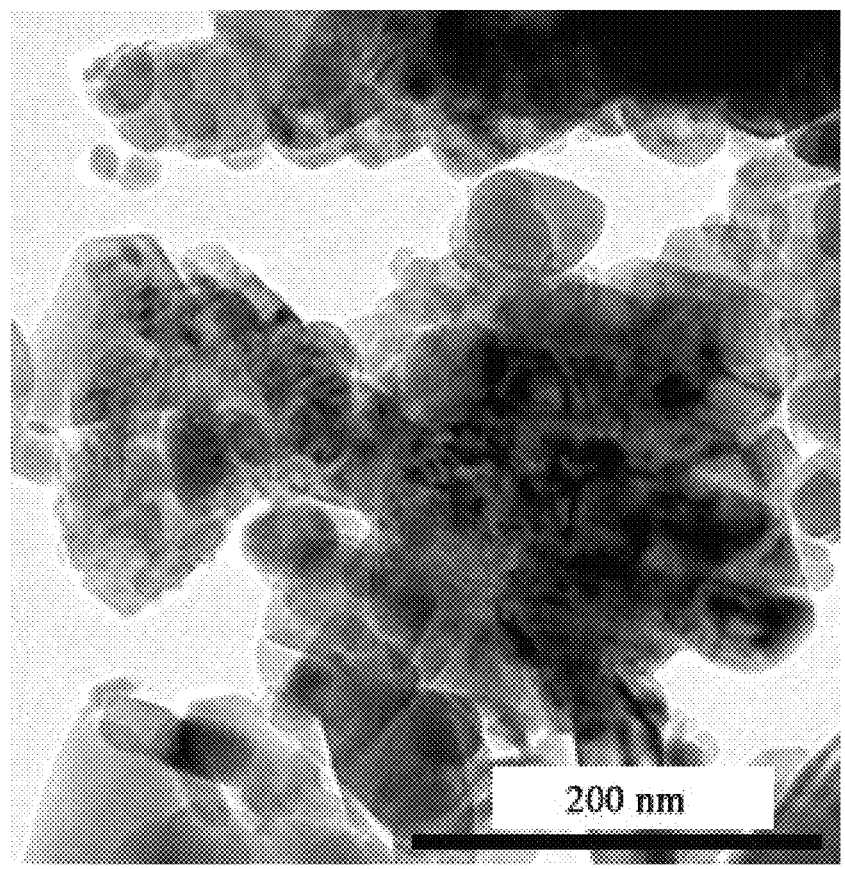
FIG. 7 is a TEM image showing the product obtained by reacting 4 h at 500° C. using TiO as a Ti source and CuCl as molten salt, wherein a mass ratio of TiO and CuCl is 1:6.

FIG. 7 is a TEM image showing the product obtained by reacting 4 h at 500° C. using TiO as a Ti source and CuCl as molten salt, wherein a mass ratio of TiO and CuCl is 1:6.

Figure 8:
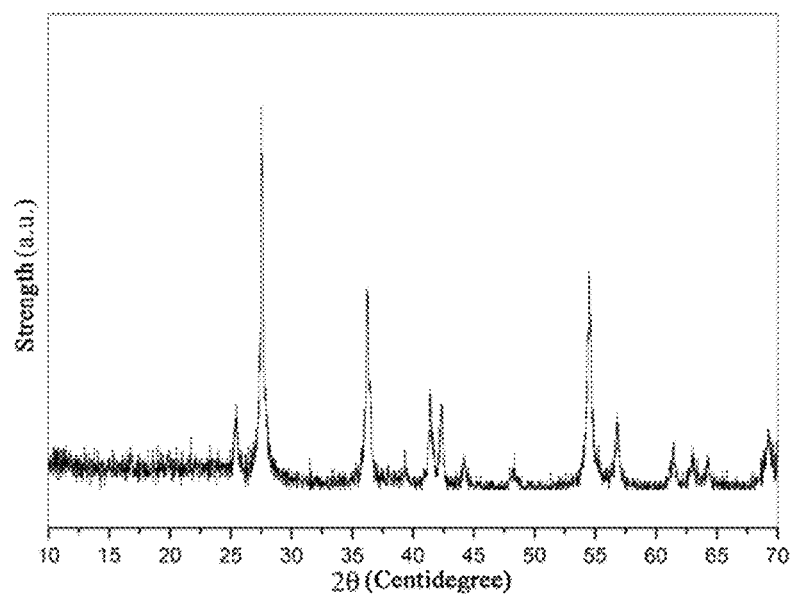
FIG. 8 is an XRD pattern showing the product obtained by reacting 6 h at 550° C. using TiCN as a Ti source and $ZnBr_2$ as molten salt, wherein a mass ratio of TiCN and $ZnBr_2$ is 1:6.

FIG. 8 is an XRD pattern showing the product obtained by reacting 6 h at 550° C. using TiCN as a Ti source and $ZnBr_2$ as molten salt, wherein a mass ratio of TiCN and $ZnBr_2$ is 1:6.

Figure 9:
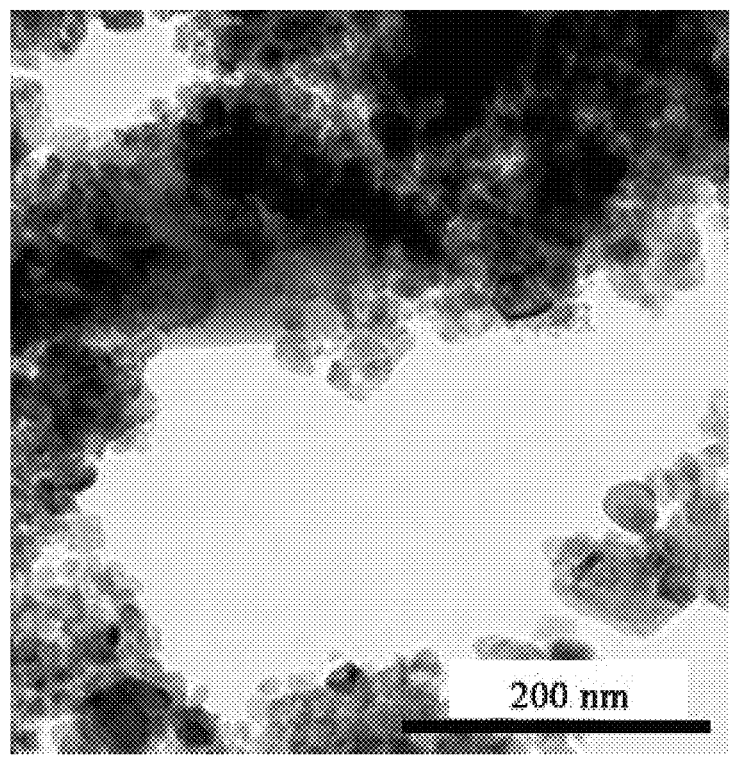
FIG. 9 is an XRD pattern showing the product obtained by reacting 6 h at 550° C. using TiCN as a Ti source and $ZnBr_2$ as molten salt, wherein a mass ratio of TiCN and $ZnBr_2$ is 1:6.

FIG. 9 is an XRD pattern showing the product obtained by reacting 6 h at 550° C. using TiCN as a Ti source and $ZnBr_2$ as molten salt, wherein a mass ratio of TiCN and $ZnBr_2$ is 1:6.

Figure 10:
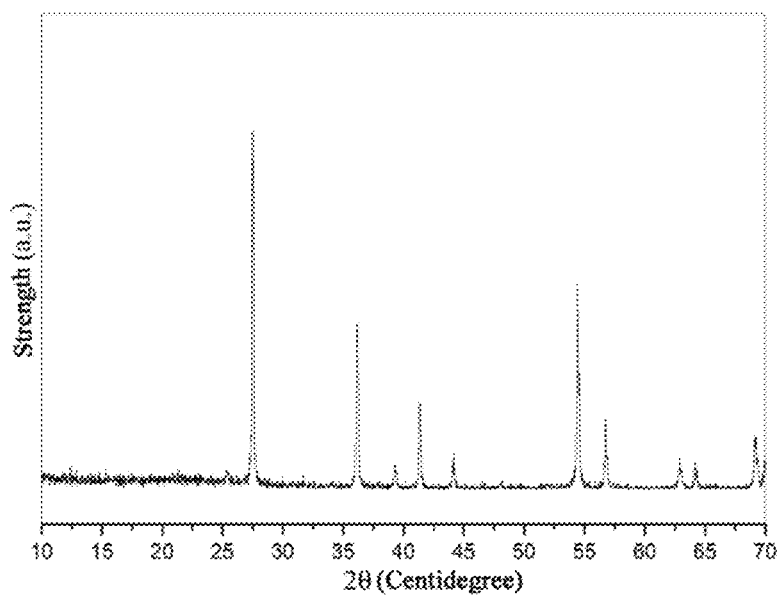
FIG. 10 is an XRD pattern showing the product obtained by reacting 6 h at 700° C. using $Ti_2O_3$ as a Ti source and $CoBr_2$ as molten salt, wherein a mass ratio between $Ti_2O_3$ and $CoBr_2$ is 1:5.

FIG. 10 is an XRD pattern showing the product obtained by reacting 6 h at 700° C. using $Ti_2O_3$ as a Ti source and $CoBr_2$ as molten salt, wherein a mass ratio between $Ti_2O_3$ and $CoBr_2$ is 1:5.

Figure 11:
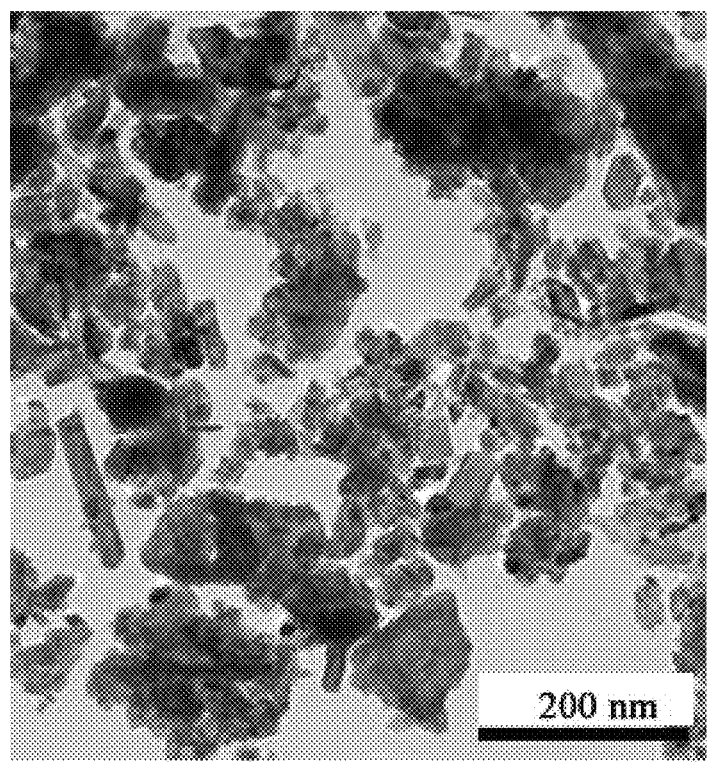
FIG. 11 is a TEM image showing the product obtained by reacting 6 h at 700° C. using $Ti_2O_3$ as a Ti source and $CoBr_2$ as molten salt, wherein a mass ratio of $Ti_2O_3$ and $CoBr_2$ is 1:5.

FIG. 11 is a TEM image showing the product obtained by reacting 6 h at 700° C. using $Ti_2O_3$ as a Ti source and $CoBr_2$ as molten salt, wherein a mass ratio of $Ti_2O_3$ and $CoBr_2$ is 1:5.

In the present invention, low-valence titanium complexes stable in air and water are used as Ti sources, transition metal halide given here is used as molten salt, upon one-step fusion reaction, reduced $Ti_{2-x}$ rich in $Ti^{3+}$ and Ov can be obtained. In the present invention, problems that conventional defect titanium dioxide preparation involves multiple steps and inflammable and explosive reducing gases or other dangerous reducing agents or oxidants are used have been addressed; furthermore, the Ti source used is stable in air and water, and the defect that organic solvents and other Ti sources that are liable to hydrolyze has been solved, which is contributive to industrialization thereof. The product obtained in the present invention has excellent visible light response performance, can be used to photo catalyze and degrade organic pollutants in waste water and waste gases, has very good sterilization and disinfection functions and can be used in water treatment and sterilization and disinfection treatment for indoor air.

Figure 12:
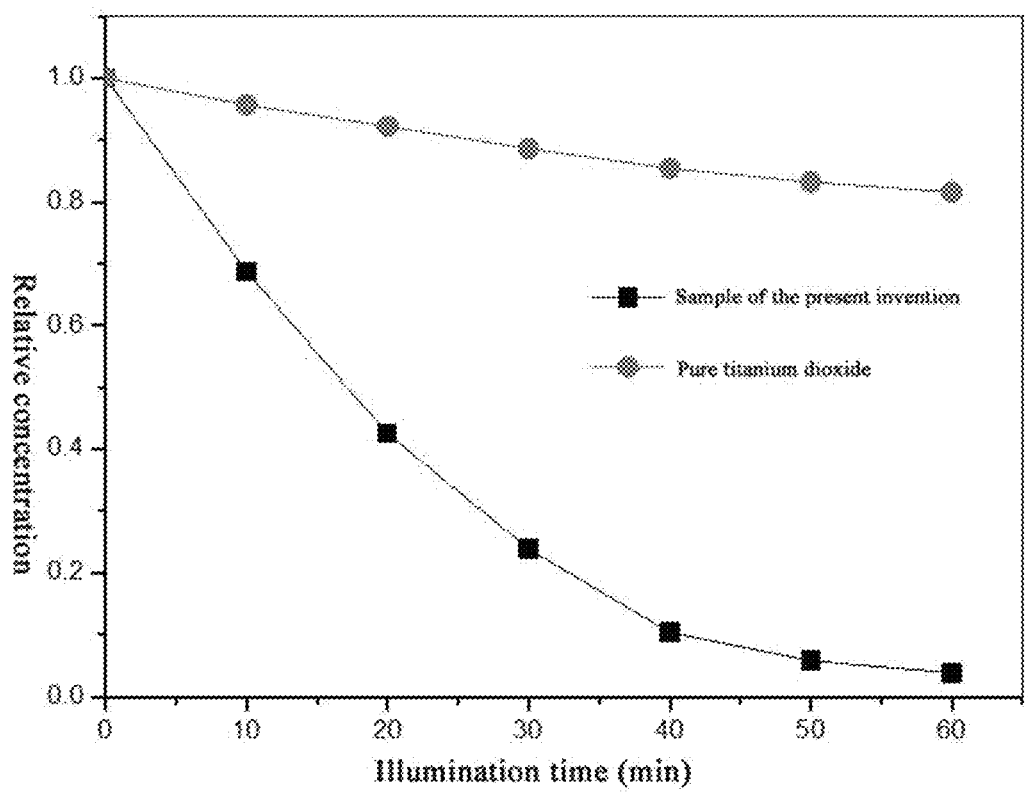
FIG. 12 is a diagram showing comparison between photo catalyzing and degrading rhodamine B with the product obtained by reacting 4 h at 450° C. using $TiH_2$ as a Ti source and CuCl as molten salt with a mass ratio between $TiH_2$ and CuCl 1:4 and with pure $TiO_2$.

FIG. 12 is a diagram showing comparison between photo catalyzing and degrading rhodamine B with the product obtained by reacting 4 h at 450° C. using $TiH_2$ as a Ti source and CuCl as molten salt with a mass ratio between $TiH_2$ and CuCl 1:4 and with pure $TiO_2$.

Figure 13:
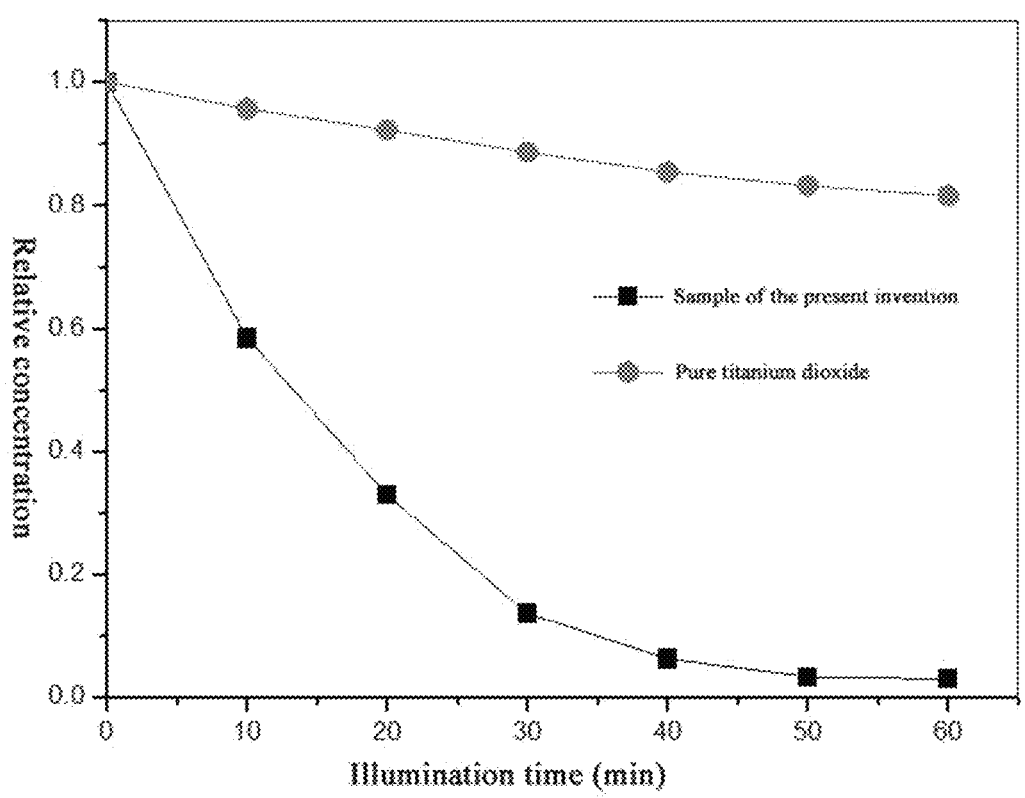
FIG. 13 is a diagram showing comparison between rhodamine B photo catalysis and degradation results by respectively the product obtained by reacting 6 h at 550° C. using TiCN as a Ti source and $ZnBr_2$ as molten salt with a mass ratio between TiCN and $ZnBr_2$ 1:6 and with pure $TiO_2$.

FIG. 13 is a diagram showing comparison between rhodamine B photo catalysis and degradation results by respectively the product obtained by reacting 6 h at 550° C. using TiCN as a Ti source and $ZnBr_2$ as molten salt with a mass ratio between TiCN and $ZnBr_2$ 1:6 and with pure $TiO_2$.

The foregoing are only some specific embodiments of the present invention, and the protection scope of the present invention is not limited to these disclosed here, any modification, equivalent replacement and improvement made by one skilled in the art in the technical range disclosed in the present invention within the spirit and principles of the present invention shall be covered in the protection scope of the present invention.

The invention claimed as:

1. A preparation method of reduced titanium dioxide photo catalyst by transition metal halide molten salt, comprising:
    using low-valence complexes stable in air and water as a Ti source, using transition metal halide as molten salt, mixing the Ti source and the molten salt as per a mole ratio, grinding, heating in air atmosphere until no less than a fusion point of the molten salt, keeping the transition metal halide in a molten state; maintaining the temperature for 2-8 h, separating by washing with water, and a reduced $TiO_{2-x}$ photo catalyst with an excellent visible response capability is obtained.

2. The preparation method of reduced titanium dioxide photo catalyst by transition metal halide molten salt according to claim 1, wherein the low-valence complexes stable in air and water are any one or combination of $TiH_2$, TiO, $Ti_2O_3$ and TiCN, the transition metal halide is any one or combination of CuCl, CuBr, $ZnBr_2$, $FeCl_3$, $CoCl_2$ and $CoBr_2$.

3. The preparation method of reduced titanium dioxide photo catalyst by transition metal halide molten salt according to claim 1, wherein the Ti source and the molten salt are mixed at a mole ratio of 1:1-1:8.

4. The preparation method of reduced titanium dioxide photo catalyst by transition metal halide molten salt according to claim 1, wherein a preparation method of reduced titanium dioxide photo catalyst by transition metal halide molten salt comprises following steps:
    step (1): weighing the Ti source and the transition metal halide, mixing and grinding fully in a mortar, transferring the same to a melting pot, putting into a muffle furnace, heating to 430-600° C. at a certain heating rate;
    step (2): maintaining the temperature for a certain period of time, turning off power supply, furnace cooling until reaching ambient temperature, taking out the melting pot, putting hot water in, treating by ultrasonic treatment or mixing; and step (3): filtering and washing a product, vacuum drying, and reduced $TiO_{2-x}$ is obtained.

5. The preparation method of reduced titanium dioxide photo catalyst by transition metal halide molten salt according to claim 4, wherein the Ti source in the step (1) is TiO, a quantity weighed is 1 g; the transition metal halide is CuCl, a quantity weighed is 4 g; the mixing and grinding time is 10-30 minutes and the heating rate is 2-10° C./min.

6. The preparation method of reduced titanium dioxide photo catalyst by transition metal halide molten salt according to claim 4, wherein in the step (2), time for maintaining the temperature is 2-8 h, and temperature of the hot water is 40-80° C.;

in the step (2), treating by ultrasonic treatment or mixing comprises: treating by ultrasonic treatment for 10-30 minutes in an ultrasonic washing machine with a frequency of 25 kHz-130 kHz or mixing magnetically and dissolving for 10-30 minutes at a mixing rate of no less than 100 r/min;

in the step (3), filtering and washing comprises: filtering the product in a common way or in vacuum, separating the product and aqueous solution of the molten salt, and washing for 3-6 times with distilled water during filtering; and in the step (3), a temperature for vacuum drying is 30-120° C. and time for vacuum drying is 2-12 h.

7. The preparation method of reduced titanium dioxide photo catalyst by transition metal halide molten salt according to claim 1, wherein the lowest temperature after heating shall be no lower than a fusion point of corresponding molten salt, no higher than a boiling point or decomposition temperature thereof; when CuCl is chosen as the molten salt, the lowest temperature after heating shall be no less than 426° C., and the highest temperature no higher than 1490° C.; when $ZnBr_2$ is chosen as the molten salt, the lowest temperature after heating shall be no less than 395° C. and the highest temperature no higher than 650° C.; time for maintaining the temperature is 2-8 h.

* * * * *